(12) United States Patent
Koike

(10) Patent No.: US 8,667,966 B2
(45) Date of Patent: Mar. 11, 2014

(54) INTUBATING ATTACHMENT AND METHOD

(76) Inventor: Hideo Koike, White Plains, NY (US)

( * ) Notice: Subject to any disclaimer, the term of this patent is extended or adjusted under 35 U.S.C. 154(b) by 521 days.

(21) Appl. No.: 12/804,983

(22) Filed: Aug. 3, 2010

(65) Prior Publication Data

US 2012/0031399 A1 Feb. 9, 2012

(51) Int. Cl.
*A61M 16/00* (2006.01)

(52) U.S. Cl.
USPC ............. 128/207.14; 128/200.24; 600/112; 600/114; 600/194

(58) Field of Classification Search
None
See application file for complete search history.

(56) References Cited

U.S. PATENT DOCUMENTS

| | | | | |
|---|---|---|---|---|
| 3,707,301 | A | * | 12/1972 | Rauls ............................. 285/9.2 |
| 4,050,466 | A | * | 9/1977 | Koerbacher ............. 128/207.14 |
| 4,416,273 | A | * | 11/1983 | Grimes .................... 128/207.16 |
| 4,683,879 | A | | 8/1987 | Williams |
| 5,024,220 | A | * | 6/1991 | Holmgreen et al. ...... 128/207.18 |
| 5,309,905 | A | * | 5/1994 | Teves ....................... 128/207.14 |
| 5,363,838 | A | | 11/1994 | George |
| 5,431,152 | A | | 7/1995 | Flam et al. |
| 5,607,386 | A | * | 3/1997 | Flam ............................. 600/120 |
| 5,645,519 | A | | 7/1997 | Lee et al. |
| 6,146,402 | A | | 11/2000 | Munoz |
| 6,196,225 | B1 | | 3/2001 | Allgeyer |
| 7,182,728 | B2 | | 2/2007 | Cubb et al. |
| 7,563,227 | B2 | | 7/2009 | Gardner |
| 7,658,708 | B2 | | 2/2010 | Schwartz et al. |
| 2005/0148821 | A1 | | 7/2005 | Berci et al. |
| 2006/0276694 | A1 | | 12/2006 | Acha Gandarias |
| 2008/0066746 | A1 | | 3/2008 | Nelson et al. |
| 2008/0312507 | A1 | | 12/2008 | Kim |
| 2009/0192355 | A1 | | 7/2009 | Mejia |

FOREIGN PATENT DOCUMENTS

WO WO2006081326 8/2006

OTHER PUBLICATIONS

Weiss, "Video-intuboscopy: a new aid to routine and difficult tracheal intubation", British Journal of Anaesthesia, 1998, vol. 80, pp. 525-527.

* cited by examiner

*Primary Examiner* — Jackie Ho
*Assistant Examiner* — Eric Bryant
(74) *Attorney, Agent, or Firm* — Robert Gorman; Gorman Law Offices

(57) ABSTRACT

An intubating attachment apparatus for use with endotracheal intubation devices comprising an elongated, generally cylindrical support module configured to accommodate a fiber optic intubation scope and at least one of an endotracheal tube or an endotracheal tube exchanger. The invention obviates the need for an attending medical professional to utilize more than one hand when advancing an endotracheal tube and/or endotracheal tube exchanger along with the fiber optic bundle of a bronchoscope into a patient.

6 Claims, 5 Drawing Sheets

INTUBATING ATTACHMENT AND METHOD

BACKGROUND OF THE INVENTION

1. Field of the Invention

This invention relates generally to medical instruments and intubating devices, and more particularly to an intubating attachment for coaxially combining existing intubating devices, such as endotracheal tubes (ETT), endotracheal tube exchangers, and fiber optic bundles of a flexible fiber optic bronchoscope together so as to provide a more easily employed operation of the aforementioned. The invention may include a hollow, thin-walled cylinder which removably receives and carries at least a portion of the aforementioned intubating devices within and/or connected to it, and may further include a handle or stabilizing feature that secures the aforementioned intubating devices together in a substantially coaxial fashion for improved ease of use by medical professionals.

2. Brief Description of the Prior Art

Endotracheal intubation is a medical procedure which concerns placement of a tube in the trachea of a patient to facilitate breathing or to permit the controlled introduction of gasses through the tube by an anesthesiologist or other medical personnel. Endotracheal intubation is normally carried out after induction of anesthesia or in emergencies, and is usually accomplished without great difficulty under direct vision with a laryngoscope by the anesthesiologist. The laryngoscope is an instrument used to examine the larynx (the uppermost end of the trachea narrowed by two surrounding vocal cords and located below the root of the tongue).

With direct laryngoscopy, the patient's neck is flexed, the head is extended and the mouth is opened wide. A laryngoscope having a rigid straight blade (commonly known as a Miller-type blade), or a rigid curved blade (commonly known as a Macintosh-type blade) is placed along the right side of the tongue, and the tongue and soft tissues of the mouth are retracted anteriorly and inferiorly to enable the larynx to be seen directly through the mouth in a straight line, instead of the normal anatomic curve around the tongue from the mouth to the larynx. The endotracheal tube (and an endotracheal tube exchanger when indicated) is then placed directly into the trachea, along this direct line of vision. Flexible fiber optic bronchoscopy may also be employed, but faces difficulty in penetration through soft tissues in search of the larynx, because of its lack of stiffness, as well as obstruction of the field of view by soft tissues, secretions, or blood. Presently, oral intubation with a flexible fiber optic bronchoscope requires a special hollow airway which is fixed in shape. Once the fiber optic bronchoscope is passed beyond the tip and into the oropharynx in search of the larynx, it has no protection from secretions, and no support or retraction to allow it to easily pass through the soft tissues and into the larynx. The same problem exists for nasal flexible fiber optic intubation, as well as for malleable fiber optic intubating devices. More importantly, it is also impossible to use these instruments with just one hand. They cannot be manipulated independently from the rest of the device, nor can they pass alone into the trachea. Moreover, anesthesiologists typically may need to employ a number of the above described devices (e.g., a fiber optic bronchoscope, an ETT and an ETT exchanger) all at the same time. Given the necessary flexibility of some of these devices, and considering that each of the devices needs to be held with a single hand, the simultaneous deployment of all of the aforementioned is limited by the number of hands of anesthesiologist, who must often involve the hands of an assistant, which limits coordinating efforts during simultaneous insertion into delicate airways.

SUMMARY OF THE INVENTION

The present invention is distinguished over the prior art in general by a providing a device that can be used with existing intubating devices in such a way as to permit the simultaneous usage of up to three such devices (e.g., a fiber optic bronchoscope, an ETT and an ETT exchanger) with one hand, thereby freeing up the second hand of a medical professional (e.g., anesthesiologist) so that they may employ the second hand for other uses, such as for manipulating a laryngoscope at the same time. In providing the above, the improved intubating attachment apparatus and method employs an elongated, generally cylindrical structure which removably engages an endotracheal tube (and/or ETT exchanger) via a frictional coaxial engagement at a frontward (second) end, and receives a fiber optic bundle of a flexible fiber optic bronchoscope at a first (rearward) end for passing through of the same within said generally cylindrical structure, and may also include a device securing means and/or a handle at the rearward end. When provisioned as such, the fiber optic bundle coaxially slides or engages through the generally cylindrical structure into (within) and along the interior tube of the ETT and/or ETT exchanger. This permits the above described intubation instruments to be both held with one hand simultaneously, and for the resulting coaxial bundle (comprising the fiber optic bundle, ETT and/or ETT exchanger) to be inserted into the mouth of a patient in a unified fashion so that the anesthesiologist may identify the larynx and advance the resulting coaxial bundle as a unit into the trachea.

It is therefore an object of the present invention to provide an improved intubating attachment apparatus and method which can be used to facilitate rapid, successful, and nonlethal oral endotracheal intubation of both awake and unconscious patients.

It is another object of the present invention to provide an improved intubating attachment apparatus and method to intubate the trachea with several intubating instruments simultaneously with a reduction in the number of hands required for holding and manipulating the same.

Another object of this invention is to provide an improved intubating attachment apparatus and method that employs a hollow tubular or cylindrical structure that carries the fiber optic bundle of a fiber optic bronchoscope within it, while simultaneously acting as a rigid guide for carrying an endotracheal tube and/or ETT exchanger fitted to it, to pass through the soft tissues of the mouth to reach the larynx.

A still further object of this invention is to provide an improved intubating attachment apparatus and method which is simple in construction, compact, inexpensive to manufacture, is readily compatible with existing intubation instrumentation, and can rapidly be used in any emergency situation with minimal preparation.

Other objects of the invention will become apparent from time to time throughout the specification and claims as hereinafter related.

DESCRIPTION OF THE PREFERRED EMBODIMENT

Figure 1:
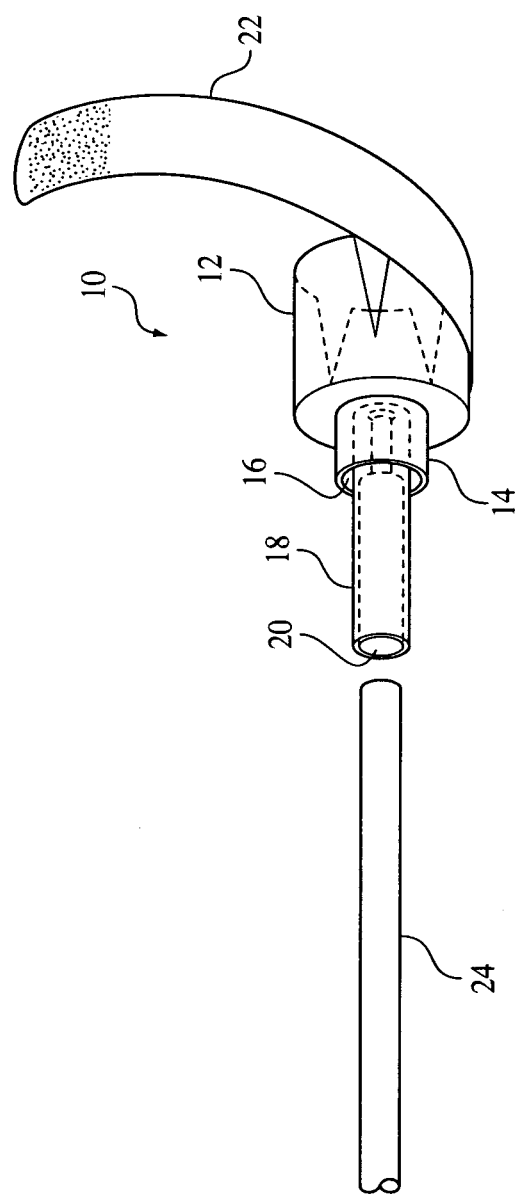
FIGS. 1 and 1A are side views in partial cross section showing the improved intubating attachment apparatus without the flexible fiber optic bundle of a fiber optic bronchoscope, but with an ETT exchanger for engagement therewith in accordance with the present invention.

At its broadest level, the present invention is directed to an intubating attachment apparatus for use with endotracheal intubation devices comprising: an elongated, generally cylindrical support module configured to accommodate a fiber optic bundle of a fiber optic intubation scope and at least one of an endotracheal tube or an endotracheal tube exchanger, with the generally cylindrical support module having a forward end, a rearward end, and a central longitudinal bore having a longitudinal axis; an elongated connecting portion disposed at the forward end for receiving and attaching the at least one of an endotracheal tube or an endotracheal tube exchanger along a substantially coaxial fashion about the longitudinal axis of said central longitudinal bore; a tube stabilization cylinder for stabilizing at least one of an endotracheal tube or an endotracheal tube exchanger, the tube stabilization cylinder extending concentrically, along the longitudinal axis of the central longitudinal bore, from the forward end of said generally cylindrical support module; a fiber optic intubation scope attachment opening at the rearward end of the module for receiving, within the central longitudinal bore, coaxially along the longitudinal axis, at least a nose portion of the fiber optic intubation scope, so as to receive an extension of the fiber optic bundle extending from the nose of the fiber optic intubation scope, generally along said longitudinal axis out through the forward end; and a fiber optic intubation scope attachment means proximate to the rearward end for releasably securing the fiber optic intubation scope nose when received by the fiber optic intubation scope attachment opening at the rearward end of the generally cylindrical support module. The inventive apparatus may, in certain embodiments, further comprise: a fiber optic scope, the nose of the fiber optic scope being releasably situated within the elongated, generally cylindrical support module and having a viewing means connected from a rearward end and wherein the fiber optic bundle is elongated, thin and flexible and transmits light from said rearward end and transmits visual images from a tip end; at least one of the flexible endotracheal tube attachment or endotracheal tube exchanger being removably affixed on the generally cylindrical support in such a way as to permit the fiber optic bundle to coaxially extend within tubes of said at least one of the flexible endotracheal tube attachment or endotracheal tube exchanger to a desired length. In some embodiments, the inventive apparatus may be constructed with a tube stabilization cylinder that varies in length between 7-8 cm along a longitudinal axis, and comprises a substantially rigid member, wherein the elongated connecting portion comprises a central aperture frictionally and slidably engaged with at least an exterior surface or an interior surface of the at least one of the aforementioned flexible endotracheal tube attachment and/or endotracheal tube exchanger so as to allow the flexible endotracheal tube attachment or endotracheal tube exchanger engaged thereon to slide longitudinally relative thereto upon the application of sufficient axial force relative to one another. In addition, the inventive apparatus may include: the fiber optic intubation scope attachment means including a band having a surface configured to frictionally engage at least a portion of the fiber optic scope upon the application of sufficient axial force relative to one another, and means to allow disengagement and disconnection thereof. In further embodiments, the inventive apparatus may include forming the elongated connecting portion from two sub-component parts which comprise an intermediate elongating neck for frictionally and slidably engaging with at least an exterior surface of said tube stabilization cylinder, and also a tube fitting portion for frictionally and slidably engaging with at least an exterior surface intermediate elongating neck and for the flexible endotracheal tube attachment or endotracheal tube exchanger engaged thereon so as to permit the same to slide longitudinally relative thereto upon the application of sufficient axial force relative to one another.

Figure 2:
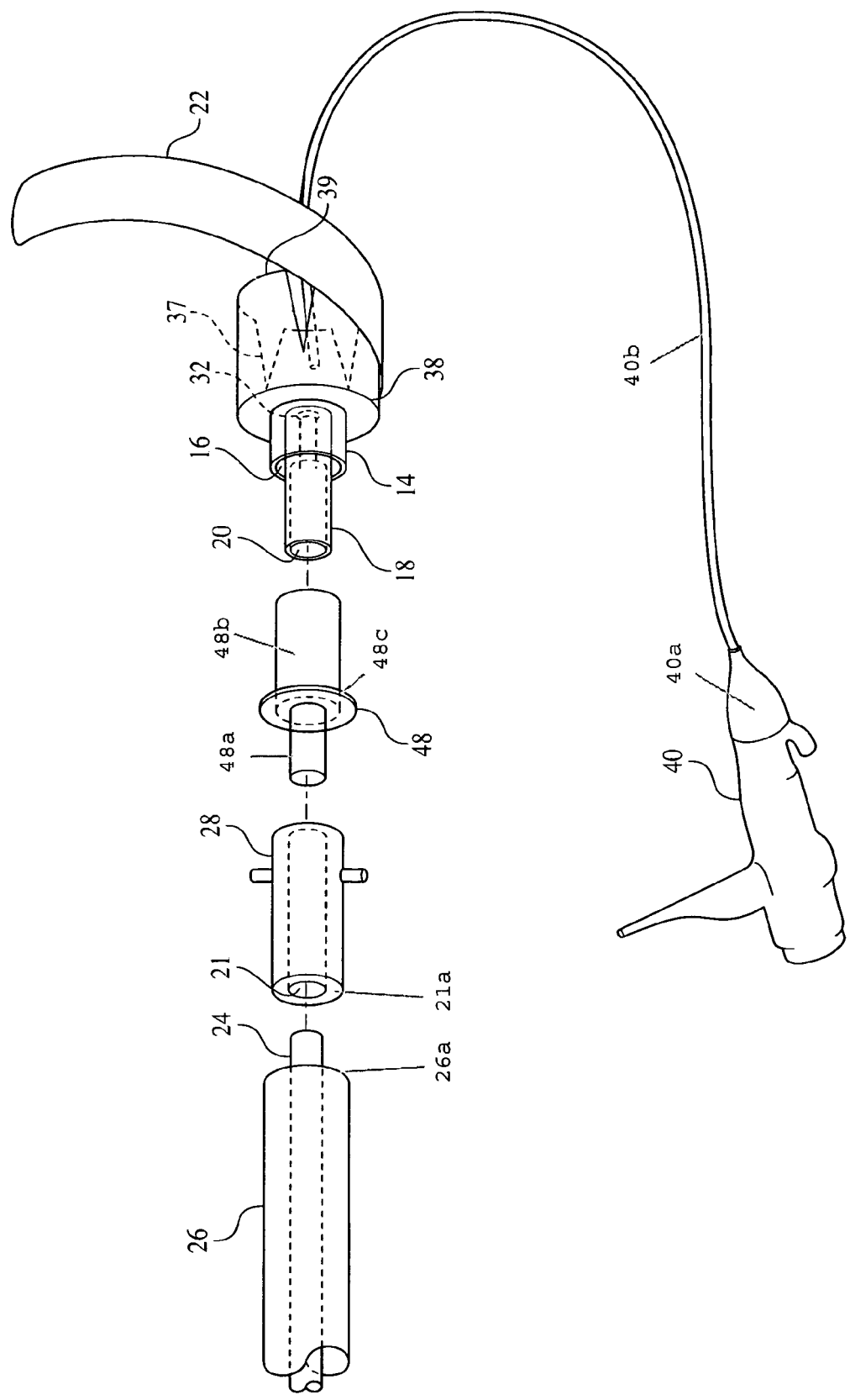
FIGS. 2 and 2A are side views in partial cross section showing the improved intubating attachment apparatus with an exploded view of an ETT, ETT exchanger, and a fiber optic bronchoscope which are to be engaged with the improved intubating attachment apparatus.

Referring now to the drawings by numerals of reference, one illustrative embodiment of the improved intubating attachment apparatus in accordance with the present invention is designated as numeral 10. As seen in FIGS. 1 and 2, the improved intubating attachment apparatus 10 comprises an elongated, generally cylindrical structure 12 which is generally a thin walled plastic tubular structure and is formed so as to have an opening at a second end or rearward end 39 for receiving flexible fiber optic bundle 40b of fiber optic bronchoscope 40, and has a frontward or first end 38 which has an attached tube stabilization cylinder 18 and an optional concentric stabilization collar 14. The second end 39 is designed for both receiving flexible fiber optic bundle 40b of fiber optic bronchoscope 40, and when the same is passed out of aperture 32 through tube stabilization cylinder 18, is also designed so as to secure a nose 40a of flexible fiber optic bronchoscope 40. The securing of nose 40a of fiber optic bronchoscope 40 substantially within generally cylindrical structure 12 may be achieved by many different means, but in one illustrative embodiment, may be effectuated by having wedge-shaped cut outs 37 radially disposed beginning at second end 39 and extending longitudinally along the walls of generally cylindrical structure 12. Thereafter, an optional securing band 22 or the like may be wrapped around the nose 40a of flexible fiber optic bronchoscope 40 and the enclosing wedge-shaped cut outs 37 the walls of generally cylindrical structure 12 to permit a securing means such as hook and loop (e.g., Velcro® marketed by Velcro USA Inc. of Manchester, N.H.), or other securing means known in the art. As can be appreciated, the exact structure and the approach to securing nose 40a of fiber optic bronchoscope 40 within generally cylindrical structure 12 are legion, and further to this point, it is also noted that even the generally cylindrical nature of generally cylindrical structure 12 need not be truly cylindrical and may be formed in differing shapes, such as conical, frustoconical, etc., all of which are explicitly contemplated within the scope of the present invention.

The endotracheal tube 26, endotracheal tube exchanger 24, and fiber optic bronchoscope 40 are of conventional construction, and therefore, are not shown or described in detail. The preferred endotracheal tube 26 and endotracheal tube exchanger 24 have standard sizes of the usual diameter for frictionally and slidably engaging with elongated connecting portion(s) 28 (also termed tube fitting portion), 48 (also termed intermediate elongating neck). Elongated connecting portion(s) 28, 48 together may comprise one unified piece (depicted hereafter in FIGS. 1A and 2A), or alternatively separately as intermediate elongating neck 48 and a tube fitting portion 28. In either case, intermediate elongating neck 48 can frictionally and slidably engage at least through rear portion 48a along at least an exterior surface of the tube stabilization cylinder 18 and for greater stabilization, rear portion 48a may fit within the interior surface 16 of optional concentric stabilization collar 14 upon the application of sufficient axial force relative to one another. Intermediate elongating neck 48 and tube fitting portion 28 are also formed so as to frictionally and slidably engage with each other upon the application of sufficient axial force relative to one another through at least an exterior surface 48a of intermediate elongating neck 48 which has a reduced diameter for frictionally sliding and engaging along an interior surface 21 inside of tube fitting portion 28 up to an optional disc collar stop 48c. When combined as such, intermediate elongating neck 48 and tube fitting portion 28 will permit flexible endotracheal tube attachment 26 to either: (i) abut an end portion 21a of tube fitting portion 28 with end portion 26a of flexible endotracheal tube attachment 26; or (ii) alternatively to slide longitudinally concentrically along an exterior surface of tube fitting portion 28 in a frictional engagement. In either case, the interior cylindrical surface of portion 48b (not depicted) can frictionally engage in a concentric fashion about the exterior surface of tube stabilization cylinder 18. Provision of such will also permit endotracheal tube exchanger 24 to slide longitudinally within the interior surface 21 of tube fitting portion 28 relative thereto upon the application of sufficient axial force relative to one another. In other embodiments, endotracheal tube exchanger 24 may also slide longitudinally from within the interior surface 21 of tube fitting portion 28 through the interior surface 20 of tube stabilization cylinder 18 to a terminus therein that will be connected with aperture 32 that is sized to permit the flexible fiber optic bundle 40b of fiber optic bronchoscope 40 to pass through the forward end 38 of generally cylindrical support module 10. In doing so, the aperture 32 will have a diameter that is wide enough to accommodate the of fiber optic bronchoscope 40 to pass through the forward end 38 of generally cylindrical support module 10, but should ideally not be wider than the diameter of tube stabilization cylinder 18 in order to avoid snagging or catching of the tip of the flexible fiber optic bundle 40b when passing the respective aperture and the successive longitudinal bores within tube stabilization cylinder 18.

Figure 1A:
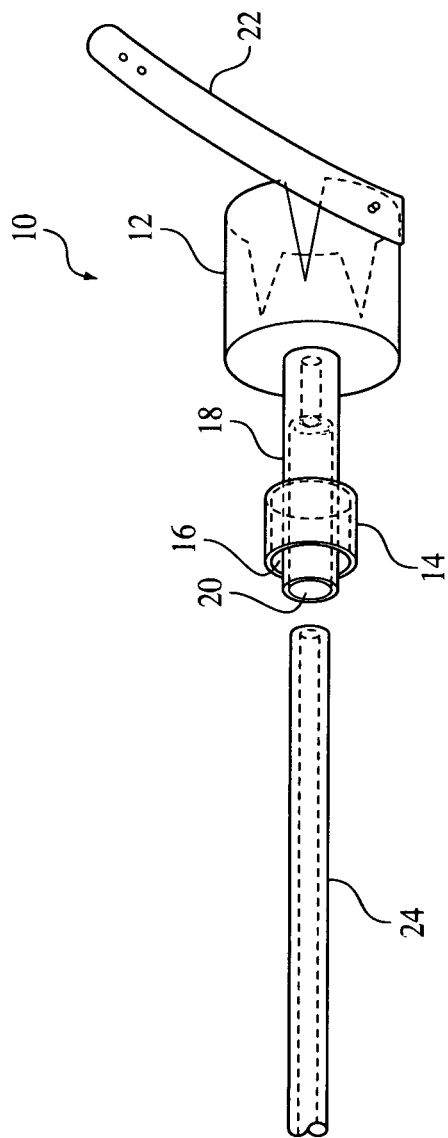
Figure 2A:
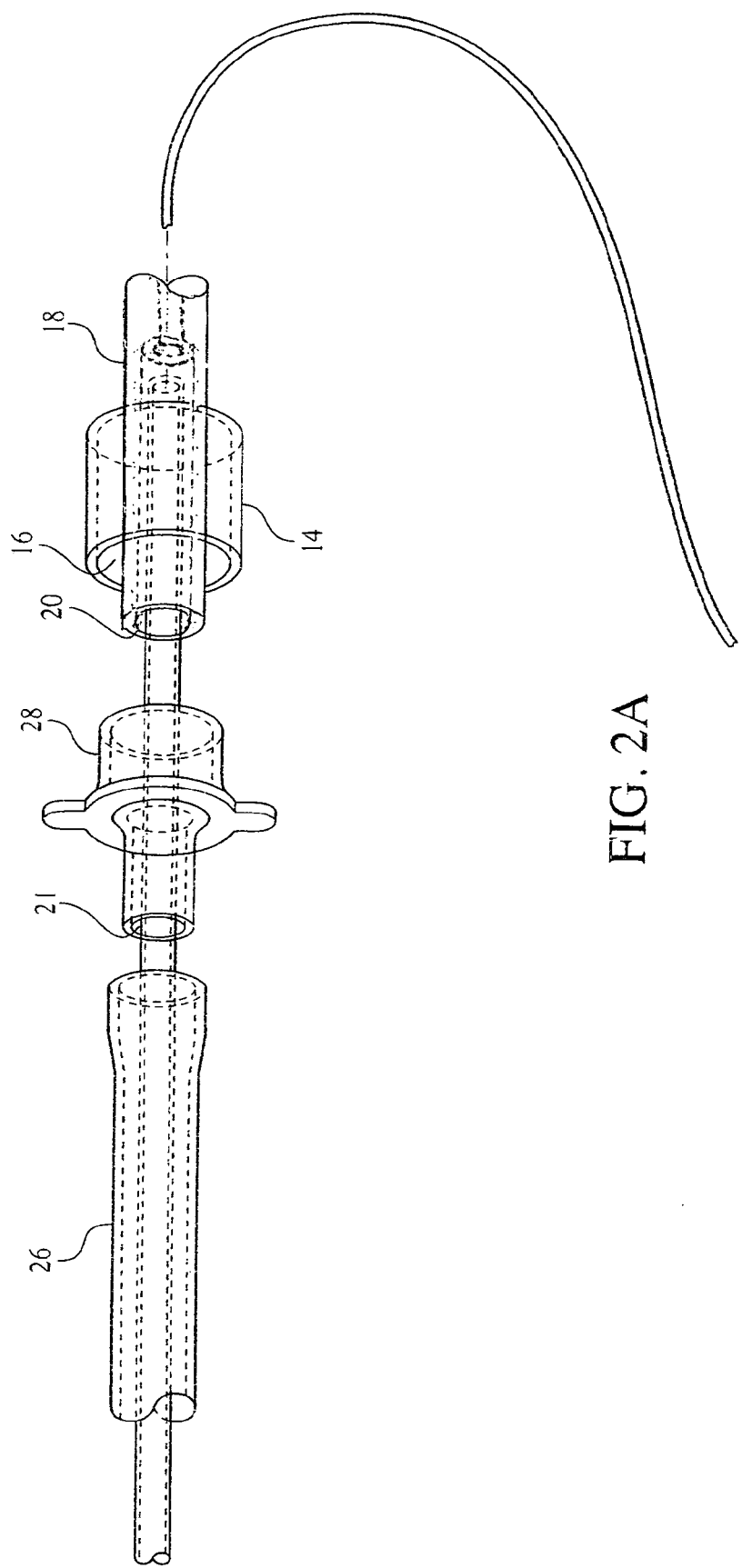

In an alternative embodiment, seen in FIGS. 1A and 2A, tube fitting portion 28 and intermediate elongating neck may be combined as one unified piece (depicted as 28 in FIG. 2A). This embodiment may be useful in situations where it is difficult to provide a tube stabilization cylinder 18 with the correct sizing, whether in manufacturing or application. In such cases it may be simpler to design tube stabilization cylinder 18 to have narrower diameter than interior surface 21 of tube fitting portion 28, particularly in situations where it may be difficult to leave enough space within tube stabilization cylinder 18 for the lumen to transition smoothly when inserted within the respective interior spaces and fittings, such as that between interior surface 21 of tube fitting portion 28 and endotracheal tube exchanger 24. To this end, optional concentric stabilization collar 14 may alternatively be situated further up along tube stabilization cylinder 18, as seen specifically in FIG. 1A, so that the diameter of tube stabilization cylinder 18 can be increased from being slightly smaller than the diameter of interior surface 21 of tube fitting portion 28 to a diameter that is measured to be just slightly smaller than the diameter of the rightmost (diametrically larger or thicker) portion of tube fitting portion 28 in FIG. 2A, which is already wide enough to accommodate tube stabilization cylinder 18. To this end, further embodiments may provide for intermediate elongating neck 48 may be dispensed with in certain applications as long as optional concentric stabilization collar 14 is sufficiently sized so as to frictionally engage flexible endotracheal tube attachment 26, endotracheal tube exchanger 24, and tube fitting portion 28 so that they slide longitudinally from within the interior surface and without the exterior surfaces of the respective parts, as long as the main object (e.g., securely holding tube fitting portion 28) of the frictional engagement of all the parts is maintained thereby.

Similarly, when all of the above described portions (e.g., flexible endotracheal tube attachment 26, tube fitting portion 28, intermediate elongating neck 48, tube stabilization cylinder 18) are fitted together in the aforementioned fashion, the respective diameters of each are sized so as to allow the snag-free insertion of both: (i) the of fiber optic bronchoscope 40 passing (via aperture 32) through the forward end 38 of generally cylindrical support module 10, tube stabilization cylinder 18, intermediate elongating neck 48, tube fitting portion 28, and then passing within the inside of endotracheal tube exchanger 24 (or alternatively, just endotracheal tube attachment 26) to the insides of a patient; and (ii) optionally, endotracheal tube exchanger 24 passing through tube fitting portion 28, intermediate elongating neck 48, into an abutment fashion within tube stabilization cylinder 18.

Thus, when provisioned in accordance with the above, the elongated connecting portion(s) 28, 48 removably engage(s), through help of the tube stabilization cylinder 18 located at the frontward end of generally cylindrical support module 10, an endotracheal tube (and/or ETT exchanger) via a frictional coaxial engagement, and receives a fiber optic bundle 40b of a fiber optic bronchoscope 40 at a rearward end for passing through of the same within said generally cylindrical structure, and may also include a device securing means and/or a handle at the rearward end. When provisioned as such, the flexible fiber optic bundle 40b coaxially slides or engages through the generally cylindrical structure into (within) and along the interior tube of the ETT and/or ETT exchanger. This permits the above described intubation instruments to be both held with one hand simultaneously, and for the resulting coaxial bundle (comprising the flexible fiber optic bundle, ETT and/or ETT exchanger) to be inserted into the mouth of a patient in a unified fashion so that the anesthesiologist may identify the larynx and advance the resulting coaxial bundle as a unit into the trachea.

Figure 3:
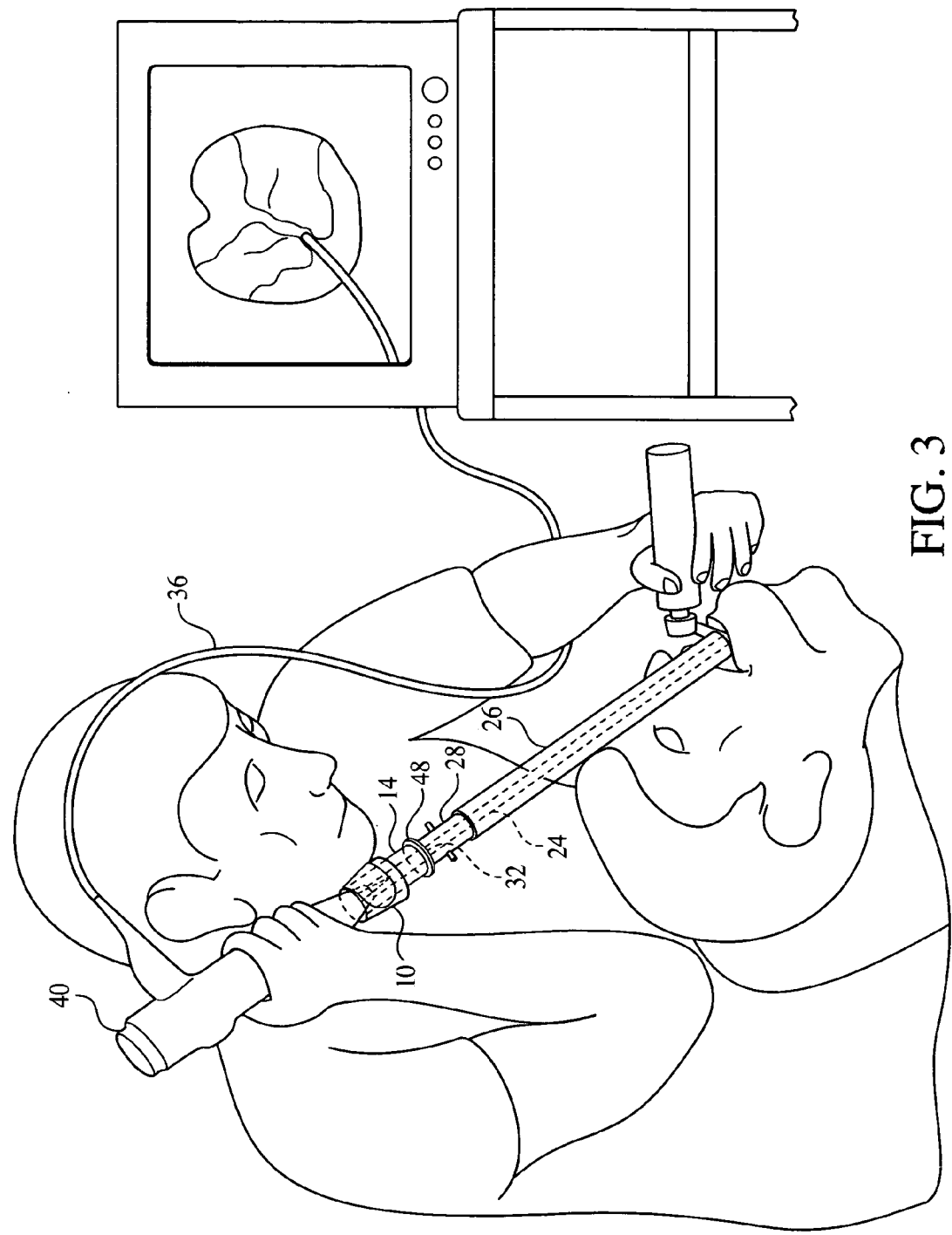
FIG. 3 is a perspective and a side view in partial cross section showing the ETT, ETT exchanger, and a fiber optic bronchoscope which are engaged with the improved intubating attachment apparatus, and showing their completed engagement illustratively employed in a clinical setting where the resulting coaxial resulting coaxial bundle is all held in one hand of a medical professional, and has been placed in the trachea of the patient, thereby freeing up the other hand of the medical professional to employ additional instrumentation, such as a laryngoscope.

The preferred fiber optic bronchoscope 40 has an external light source which is connected by a fiber optic cable to a light source (not shown), and has an eyepiece at its outer end for viewing when in use, through the same and/or through a viewing output connection 36 to a display screen, as depicted in FIG. 3, for displaying the image seen through the flexible fiber optic bundle 40b.

To assemble all of the above, the portions previously described in FIGS. 1 and 2 are secured in conformity therewith, and, as seen in FIG. 3, the flexible fiber optic bundle 40b of the fiber optic bronchoscope 40 is passed through the rearward end of generally cylindrical support module 10 until the nose 40a reaches the frontward area 38, and is in general longitudinal alignment with aperture 32 (and the center bore of tube stabilization cylinder 18) until the tip of flexible fiber optic bundle 40b has snaked all the way through tube stabilization cylinder 18, intermediate elongating neck 48, intermediate elongating neck 48, tube fitting portion 28, and then passes within the inside of endotracheal tube exchanger 24 (or alternatively, just endotracheal tube attachment 26) so that it can be inserted to the patient's airway as a unit. Thereafter, optional securing band 22 or the like is wrapped around the nose 40a of fiber optic bronchoscope 40 and the enclosing wedge-shaped cut outs 37 the walls of generally cylindrical structure 12 to conclude the securing of the parts.

After all of the above has been properly placed, all of the intubation instruments can then be both held with one hand simultaneously, and the resulting coaxial bundle (comprising the fiber optic bundle, ETT and/or ETT exchanger) can be inserted into the mouth of a patient in a unified fashion so that the anesthesiologist may identify the larynx and advance the resulting coaxial bundle as a unit into the trachea, and thereby freeing up the hands of the anesthesiologist when compared with known approaches.

While this invention has been described fully and completely with special emphasis upon preferred embodiments, it should be understood that within the scope of the appended claims the invention may be practiced otherwise than as specifically described herein.

I claim:

1. An intubating attachment apparatus for use with endotracheal intubation devices comprising:
    an elongated cylindrical structure configured to receive a fiber optic bundle of a fiber optic intubation scope and to provide secure engagement of at least one of an endotracheal tube or an endotracheal tube exchanger, said elongated cylindrical structure having a forward end, a rearward end, and a central longitudinal bore having a longitudinal axis;
    an elongated connecting portion, disposed at said forward end of said elongated cylindrical structure, for receiving and attaching said at least one of an endotracheal tube or an endotracheal tube exchanger along a coaxial fashion about said longitudinal axis of said central longitudinal bore, so as to provide for said secure engagement of at least one of an endotracheal tube or an endotracheal tube exchanger by said elongated cylindrical structure;
    a tube stabilization cylinder for stabilizing, via said elongated connecting portion, at least one of an endotracheal tube or an endotracheal tube exchanger as attached to said elongated connecting portion, said tube stabilization cylinder extending concentrically, along said longitudinal axis of said central longitudinal bore, from said forward end of said elongated cylindrical structure;
    a fiber optic intubation scope attachment opening at the rearward end of said elongated cylindrical structure for receiving, within said central longitudinal bore, coaxially along said longitudinal axis, at least a nose portion of said fiber optic intubation scope, so as to receive an extension of said fiber optic bundle coaxially extending from said nose of said fiber optic intubation scope, along said longitudinal axis out through said forward end of said elongated cylindrical structure; and
    a fiber optic intubation scope attachment means proximate to said rearward end of said elongated cylindrical structure for releasably securing said fiber optic intubation scope nose when received by said fiber optic intubation scope attachment opening at the rearward end of said elongated cylindrical structure;
    whereby said nose portion of said fiber optic intubation scope, said fiber optic bundle of said fiber optic intubation scope and said at least one of an endotracheal tube or an endotracheal tube exchanger are all collectively enclosed by a continuous, fitted tube portions means for one handed control and stabilization, wherein:
    said continuous, fitted tube portions means for one handed control and stabilization comprises at least said elongated cylindrical structure, said elongated connecting portion, and said tube stabilization cylinder for stabilizing, wherein:
    said elongated cylindrical structure, said elongated connecting portion, and said tube stabilization cylinder for stabilizing each have an internal diameter for frictionally slidably engaging for forming a continuous connection of said central longitudinal bore about said longitudinal axis for continuous enclosure of at least said fiber optic bundle, and configured for inserting and advancing said fiber optic bundle of a fiber optic intubation scope and said at least one of an endotracheal tube or an endotracheal tube as a unified coaxial bundle unit into patient mouths.

2. The apparatus of claim 1 wherein said elongated connecting portion comprises a tube fitting portion for frictionally and slidably engaging with at least said one of a flexible endotracheal tube attachment or endotracheal tube exchanger by sliding longitudinally relative thereto upon the application of sufficient axial force relative to one another.

3. The apparatus of claim 2 further comprising:
    the fiber optic intubation scope, said nose of said fiber optic intubation scope being releasably situated within said elongated cylindrical structure and having a viewing means connected from a rearward end and wherein said fiber optic bundle is elongated, thin and flexible and transmits light from said rearward end and transmits visual images from a tip end;
    at least one of said flexible endotracheal tube attachment or endotracheal tube exchanger being removably affixed on said elongated cylindrical structure in such a way as to permit said fiber optic bundle to coaxially extend, through said fitted tube portion means for enclosement of said fiber optic bundle about said longitudinal axis of said longitudinal bore of said at least one of said flexible endotracheal tube attachment or endotracheal tube exchanger to a desired length.

4. The apparatus of claim 3 wherein:
    said tube stabilization cylinder varies in length between 7-8 cm along a longitudinal axis, and comprises a rigid member, and wherein said elongated connecting portion comprises a central aperture frictionally and slidably engaged with at least an exterior surface or an interior surface of said at least one of said flexible endotracheal tube attachment or endotracheal tube exchanger so as to allow said flexible endotracheal tube attachment or endotracheal tube exchanger engaged thereon to slide longitudinally relative thereto upon the application of sufficient axial force relative to one another.

5. The apparatus of claim 4 wherein:
    said fiber optic intubation scope attachment means of said elongated cylindrical structure has wedge shaped cut outs radially disposed and extending longitudinally along walls of said elongated cylindrical structure
    and wherein said fiber optic intubation scope attachment means comprises, situated on said elongated cylindrical structure, at least a handle means for one handed control of said intubating attachment apparatus, wherein said handle means for one handed control of said intubating attachment apparatus includes a securing band for securely wrapping said wedge-shaped cut outs around said nose of said fiber optic scope within said elongated cylindrical structure; and wherein:
    said viewing means comprises a display screen.

6. The apparatus of claim 5 wherein:

said elongated connecting portion further comprises an intermediate elongating neck for frictionally and slidably engaging with at least an exterior surface of said tube stabilization cylinder and an exterior surface of said tube fitting portion so as to slide longitudinally relative thereto upon the application of sufficient axial force relative to one another, and wherein said securing band is a hook and loop securing.

* * * * *